(12) United States Patent
Feaster et al.

(10) Patent No.: US 8,377,379 B2
(45) Date of Patent: *Feb. 19, 2013

(54) LATERAL FLOW ASSAY DEVICE

(75) Inventors: Shawn R. Feaster, Duluth, GA (US); Kaiyuan Yang, Cumming, GA (US); Ning Wei, Roswell, GA (US); Chibueze O. Chidebelu-Eze, Atlanta, GA (US); James M. Takeuchi, Roswell, GA (US); Rosann M. Kaylor, Cumming, GA (US); Enrico L. DiGiammarino, Lindenhurst, IL (US); Jeffrey E. Fish, Winston-Salem, NC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1919 days.

This patent is subject to a terminal disclaimer.

(21) Appl. No.: 11/640,435

(22) Filed: Dec. 15, 2006

(65) Prior Publication Data

US 2008/0145272 A1 Jun. 19, 2008

(51) Int. Cl.
*G01N 30/96* (2006.01)
(52) U.S. Cl. ......................................................... 422/69
(58) Field of Classification Search .................... 422/69
See application file for complete search history.

(56) References Cited

U.S. PATENT DOCUMENTS

| | | |
|---|---|---|
| 4,503,856 A | 3/1985 | Cornell et al. |
| 4,517,978 A | 5/1985 | Levin et al. |
| 4,742,011 A | 5/1988 | Blake et al. |
| 4,743,560 A | 5/1988 | Campbell et al. |
| 4,835,099 A | 5/1989 | Mize et al. |
| 4,889,816 A | 12/1989 | Davis et al. |
| 4,904,583 A | 2/1990 | Mapes et al. |
| 4,920,046 A | 4/1990 | McFarland et al. |
| 4,954,435 A | 9/1990 | Krauth |
| 4,956,302 A | 9/1990 | Gordon et al. |
| 4,978,625 A | 12/1990 | Wagner et al. |
| 4,980,298 A | 12/1990 | Blake et al. |

(Continued)

FOREIGN PATENT DOCUMENTS

| | | |
|---|---|---|
| EP | 1 389 445 | 2/2004 |
| WO | WO 02/10754 | 2/2002 |

(Continued)

OTHER PUBLICATIONS

PCT Search Report, Dec. 17, 2008.

*Primary Examiner* — Lore Jarrett
(74) *Attorney, Agent, or Firm* — Dority & Manning, P.A.

(57) ABSTRACT

A lateral flow assay device includes a housing, and a test strip disposed within the housing having a membrane with a detection region and a collection region. A sample meter includes a first end for absorption of a test sample, and a storage section that receives and stores at least a component of the test sample. An opening in the housing is sized for insertion of the sample meter into the housing such that the storage section of the sample meter is disposed adjacent the collection region of the membrane. The test sample component is transferable from the storage section to the collection region for subsequent migration to the detection region. An activatable isolation mechanism is provided within the housing and is disposed so as to isolate portions of the sample meter storage section upon activation thereof such that a defined length of the storage section is presented to the collection region of the membrane.

21 Claims, 5 Drawing Sheets

U.S. PATENT DOCUMENTS

| | | | |
|---|---|---|---|
| 5,073,340 | A | 12/1991 | Covington et al. |
| 5,075,078 | A | 12/1991 | Osikowicz et al. |
| 5,120,643 | A | 6/1992 | Ching et al. |
| 5,149,622 | A | 9/1992 | Brown et al. |
| 5,185,127 | A | 2/1993 | Vonk |
| 5,208,143 | A | 5/1993 | Henderson et al. |
| 5,275,785 | A | 1/1994 | May et al. |
| 5,320,607 | A | 6/1994 | Ishibashi |
| 5,368,047 | A | 11/1994 | Suzuki et al. |
| 5,415,994 | A | 5/1995 | Imrich et al. |
| 5,416,000 | A | 5/1995 | Allen et al. |
| 5,423,989 | A | 6/1995 | Allen et al. |
| 5,428,690 | A | 6/1995 | Bacus et al. |
| 5,487,748 | A | 1/1996 | Marshall et al. |
| 5,573,919 | A | 11/1996 | Kearns et al. |
| 5,591,645 | A | 1/1997 | Rosenstein |
| 5,602,040 | A | 2/1997 | May et al. |
| 5,610,077 | A | 3/1997 | Davis et al. |
| 5,622,871 | A | 4/1997 | May et al. |
| 5,656,503 | A | 8/1997 | May et al. |
| 5,662,127 | A | 9/1997 | De Vaughn |
| 5,714,389 | A | 2/1998 | Charlton et al. |
| 5,788,863 | A | 8/1998 | Milunic |
| 5,798,273 | A | 8/1998 | Shuler et al. |
| 5,945,281 | A | 8/1999 | Prabhu |
| 5,951,493 | A | 9/1999 | Douglas et al. |
| 5,989,924 | A | 11/1999 | Root et al. |
| 5,989,926 | A | 11/1999 | Badley et al. |
| 5,998,221 | A | 12/1999 | Malick et al. |
| 6,008,059 | A * | 12/1999 | Schrier et al. .......... 436/518 |
| 6,057,165 | A | 5/2000 | Mansour |
| 6,077,669 | A | 6/2000 | Little et al. |
| 6,130,100 | A | 10/2000 | Jobling et al. |
| 6,133,048 | A | 10/2000 | Penfold et al. |
| 6,140,136 | A | 10/2000 | Lee |
| 6,151,110 | A | 11/2000 | Markart |
| 6,156,271 | A | 12/2000 | May |
| 6,187,269 | B1 | 2/2001 | Lancesseur et al. |
| 6,194,220 | B1 | 2/2001 | Malick et al. |
| 6,197,598 | B1 | 3/2001 | Schrier et al. |
| 6,274,324 | B1 | 8/2001 | Davis et al. |
| 6,294,391 | B1 | 9/2001 | Badley et al. |
| 6,352,862 | B1 | 3/2002 | Davis et al. |
| 6,399,398 | B1 | 6/2002 | Cunningham et al. |
| 6,524,864 | B2 | 2/2003 | Fernandez de Castro |
| 6,627,459 | B1 | 9/2003 | Tung et al. |
| 6,653,149 | B1 | 11/2003 | Tung et al. |
| 6,669,908 | B2 | 12/2003 | Weyker et al. |
| RE38,430 | E | 2/2004 | Rosenstein |
| 6,837,858 | B2 | 1/2005 | Cunningham et al. |
| 6,951,631 | B1 | 10/2005 | Catt et al. |
| 7,044,919 | B1 | 5/2006 | Catt et al. |
| 7,052,831 | B2 | 5/2006 | Fletcher et al. |
| 7,618,810 | B2 * | 11/2009 | Yang et al. ............ 435/286.5 |
| 2002/0042149 | A1 | 4/2002 | Butlin et al. |
| 2002/0045273 | A1 | 4/2002 | Butlin et al. |
| 2004/0151632 | A1 | 8/2004 | Badley et al. |
| 2004/0161859 | A1 | 8/2004 | Guo et al. |
| 2005/0029924 | A1 | 2/2005 | Okai et al. |
| 2005/0036148 | A1 | 2/2005 | Phelan et al. |
| 2005/0037510 | A1 | 2/2005 | Sharrock et al. |
| 2005/0109951 | A1 | 5/2005 | Fish et al. |
| 2005/0112635 | A1 | 5/2005 | Gentle et al. |
| 2006/0127924 | A1 | 6/2006 | Hellyer et al. |
| 2006/0240569 | A1 | 10/2006 | Goldenbaum et al. |
| 2007/0019502 | A1 | 1/2007 | Foley et al. |
| 2010/0015658 | A1 * | 1/2010 | Yang et al. ............... 435/29 |

FOREIGN PATENT DOCUMENTS

| | | | |
|---|---|---|---|
| WO | WO 2005/045408 | | 5/2005 |

* cited by examiner

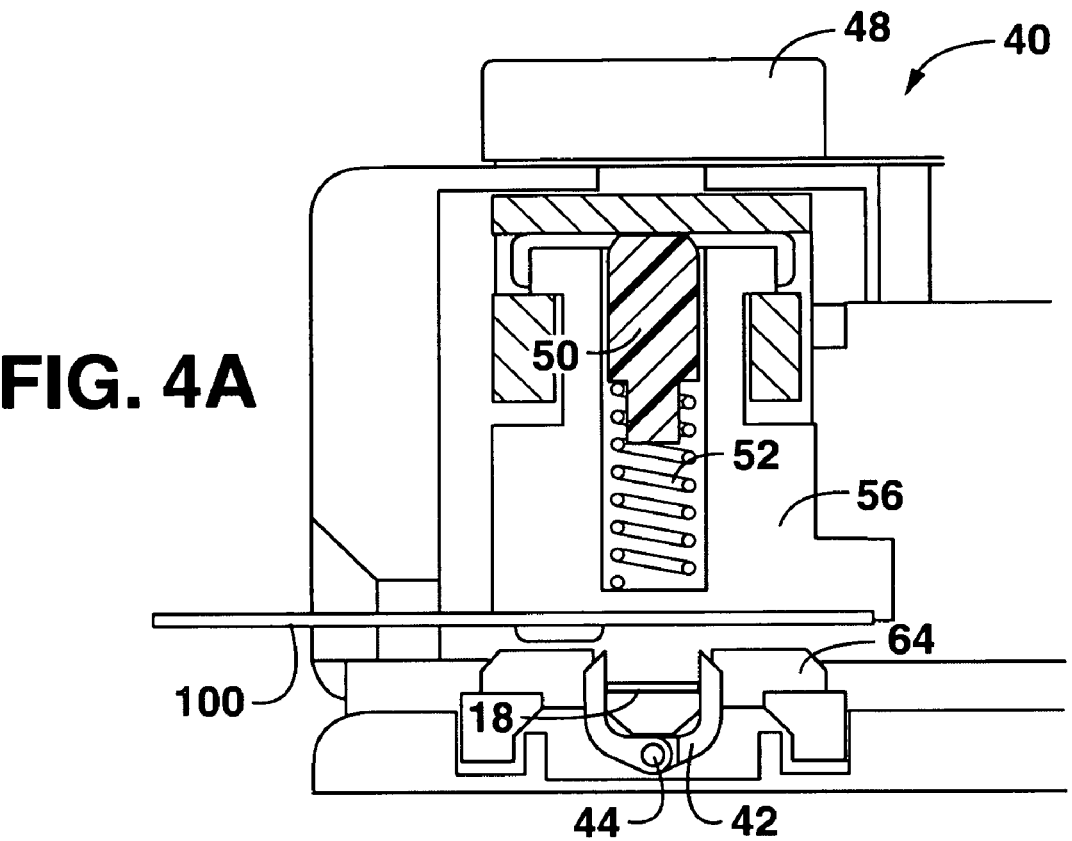
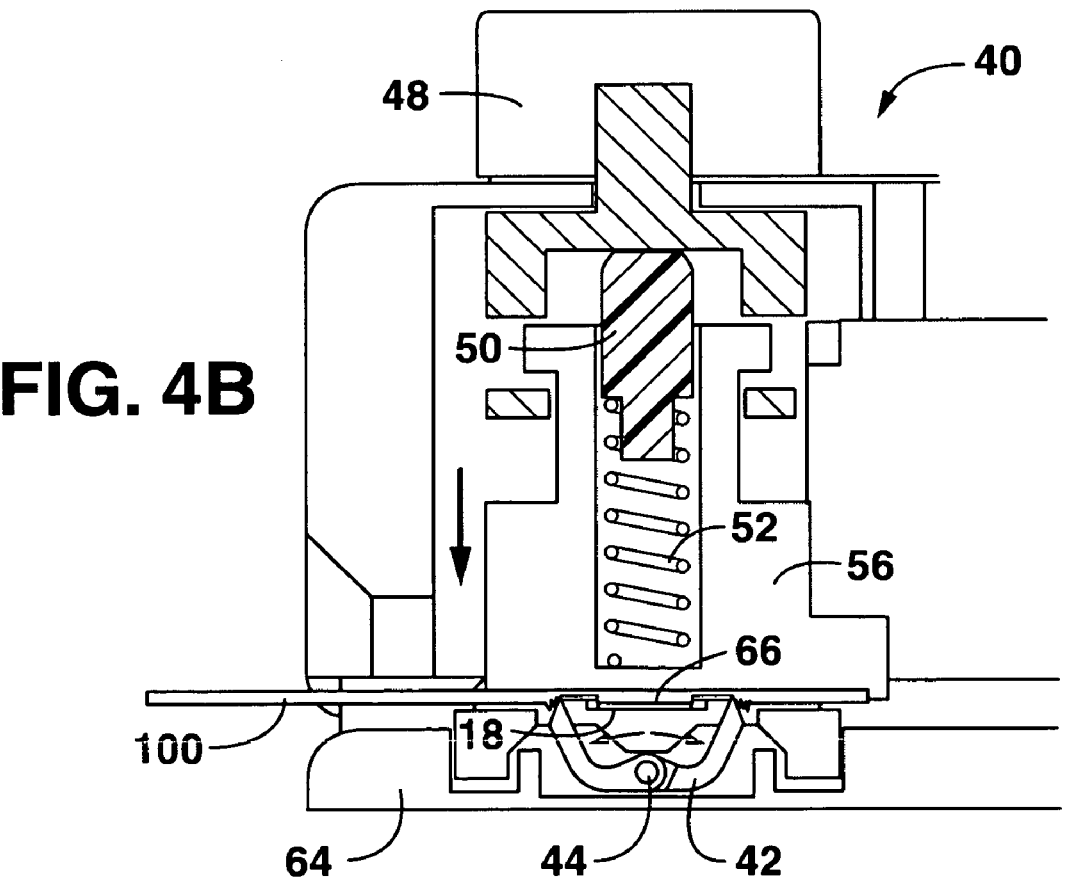

LATERAL FLOW ASSAY DEVICE

BACKGROUND OF THE INVENTION

Test strips are often used for qualitative and quantitative analysis of blood components or other fluids. With the lateral flow method, a spatial separation is defined in the strips between the sample application area and detection zone. Most conventional lateral flow strips are designed for test samples that are readily available in large quantities (e.g., urine). However, when the test sample is blood, the collection of a large sample may cause undue pain to the patient. Thus, one technique that has been utilized to accommodate smaller test sample volumes is to "spot" the sample directly on the membrane surface of the test strip. Thereafter, a diluent is used to wash away the test sample and carry it to the detection zone. Unfortunately, variations associated with sample transfer and diffusion of the sample to the membrane result in a flow that is largely uncontrolled and uneven before reaching the detection zone. This may have an adverse effect on the accuracy of the device because the amount of analyte and/or label captured across the detection zone is not consistent at the time of measurement.

In addition, various tests on blood samples require separation of the red blood cell components from the sample to obtain plasma or serum that is essentially free of red blood cells. The sample can then be used in various assays without interference from red blood cell components. In this regard, filter arrangements have been proposed for production of serum or plasma from whole blood. For example, U.S. Pat. No. 5,423,989 describes a membrane filtering arrangement with a first coarse membrane coated with a fibrous protein and a second fine membrane for removing red blood cells from a test sample.

As such, a need currently exists for a simple and efficient technique for metering and filtering a low volume blood test sample such that a known volume of blood plasma or serum may be easily transferred to a detection zone of a lateral flow assay device.

SUMMARY OF THE INVENTION

Objects and advantages of the invention will be set forth in part in the following description, or may be obvious from the description, or may be learned through practice of the invention.

In accordance with one embodiment of the present invention, a diagnostic lateral flow assay device is provided for detecting the presence of an analyte within a test sample. The device and associated method of use are particularly well suited for use with relatively small blood samples of generally less than 10 microliters, and aspects of the invention will be described herein by reference to a blood sampling device and method. It should be appreciated, however, that this is for illustrative purposes only, and that the device is not limited to blood sampling.

The lateral flow assay device has a housing and a test strip within the housing. The test strip includes a membrane having a collection region that receives the test sample, and a detection region. A blood sample meter is provided having a first end for absorption of a blood sample, and may include a filter section adjacent the first end that filters red blood cell components from the blood sample. A storage section adjacent the filtering section receives the plasma or serum from the filtering section. An opening in the housing is sized for insertion of the sample meter into the housing such that the storage section of the sample meter is disposed adjacent to the collection region of membrane.

In order to provide a precisely determined volume of the sample (i.e., plasma or serum) to the test strip, the assay device includes an internal mechanism configured to isolate a specific section of the sample meter (e.g., by scoring and scraping) so that only a well-defined section of the test meter is presented to the collection region of the test strip. This defined section may be, for example, a 5 mm length of the sample meter storage section. This section is saturated with the sample fluid and thus, based on the absorbent capacity of the sample meter, contains a precisely determined amount of the sample fluid. Once the sample meter has been isolated (e.g. scraped), the defined length of storage section is brought into fluid communication with the collection region of the membrane (by direct contact or through an intermediary member) and the filtered plasma or serum is transferred from the defined length of storage section to the collection region of the membrane for subsequent migration to the detection region. This transfer of plasma or serum typically would occur through simple capillary action, but may also be caused to occur through other means. For example, a diluent may be supplied to the collection region to facilitate flow of the test sample from the collection region to the detection region of the membrane.

In a particular embodiment suited for sampling and testing blood, the sample meter includes a separation membrane material attached to a storage membrane with an overlap between the membranes. The separation membrane serves to drawn in the blood sample (e.g., through capillary action) and separate out red blood cell components. The resulting filtered plasma or serum is transferred to the storage membrane. It should be appreciated that the sample meter is not limited by dimensions or shape. For example the separation membrane may have a length of between about 3 to about 12 mm, and the overlap region between the separation and storage membranes may be between about 1 mm to about 3 mm. The storage membrane may have a length of between about 10 mm to about 40 mm. In a particular embodiment, the sample meter is an elongated member having a width of between about 1 mm to about 5 mm, and a length of between about 25 mm to about 40 mm. The separation membrane may extend to the first end of the sample meter, and the storage membrane may extend to an opposite second end of the sample meter.

To add structural rigidity to the sample meter, it may be desired to attach the filter and storage membranes to a backing strip. This backing strip may be generally transparent so that migration of the blood plasma or serum to the storage section of the meter may be observed through the backing strip material.

The assay device may incorporate an internal source of diluent that is applied so as to flow to the collection region subsequent to insertion of the sample meter into the assay housing. For example, the diluent may be stored in a rupturable container or pouch within the housing. Means may be provided for rupturing or otherwise breaching this container subsequent to or coinciding with insertion and scraping of the sample meter within the housing. For example, a push-button, slide mechanism, or other manually actuated device may be configured with the assay housing whereby, upon actuation of the mechanism, a point or blade configured on the mechanism pierces the container causing the diluent to flow to the collection region of the membrane. The mechanism may also serve to compress the container so as to force the diluent therefrom towards the direction of the membrane. This mechanism may be configured to work in conjunction with the sample meter scraping mechanism, or may be a separate mechanism. For example, the scraping mechanism may be actuated by a first manual device (e.g. push-button or slide) with the diluent releasing mechanism actuated by a separate manual device. Alternatively, the two mechanisms may be actuated by a single manual device. It should be appreciated that any number of manually actuated devices may be readily configured by those skilled in the art for this purpose, and all such devices are within the scope and spirit of the invention.

In an alternate embodiment, the diluent may be supplied from an external source, with the assay housing configured for fluid communication with this external source. For example, the diluent may be supplied in a disposable, squeezable container having a nozzle that communicates with a port on the assay housing. This port may be configured to internally direct the diluent directly to the collection region of the membrane.

The invention also encompasses all variations of methods of using the blood sample meters and associated assay devices, as described above.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIGS. 4A and 4B are additional cross-sectional views of a scraping mechanism that may be used in an assay device according to the invention.

Figure 1:
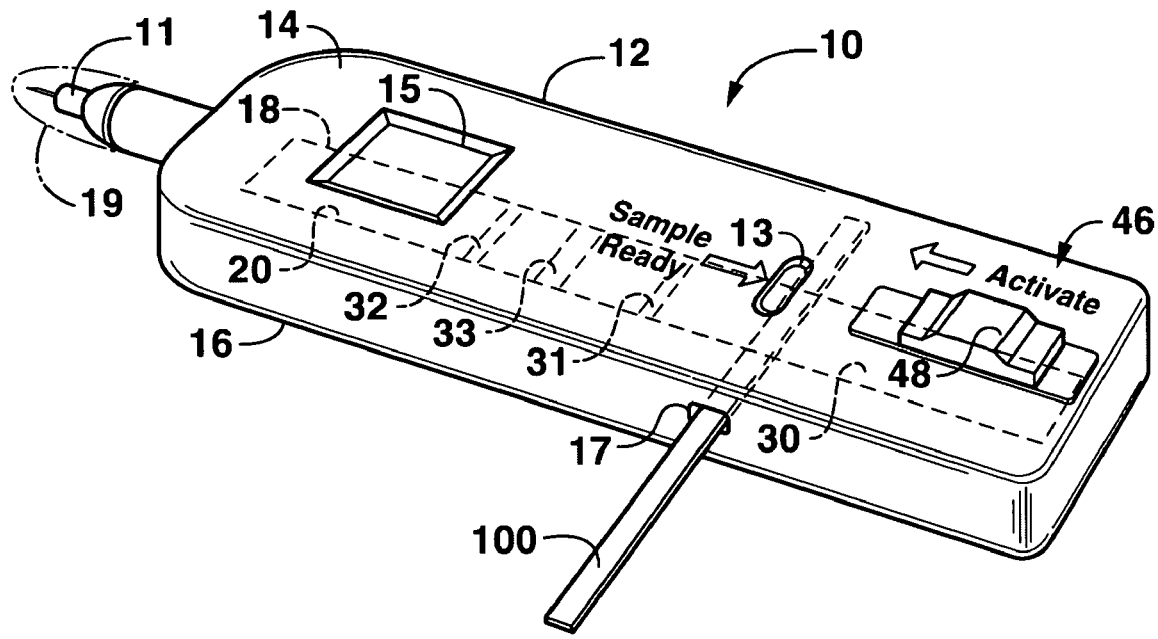
FIG. 1 is a perspective view of a lateral flow assay device that incorporates aspects of the present invention.

Repeat use of reference characters in the present specification and drawings is intended to represent same or analogous features or elements of the invention.

DETAILED DESCRIPTION OF
REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

Exemplary Embodiments

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is directed generally to a diagnostic method and device for detecting the presence of an analyte within a blood test sample. The device and associated method of use are particularly well suited for use with relatively small blood samples of generally less than 10 microliters. Referring to the figures in general, the device is embodied in a particular embodiment as a lateral flow assay device 10 having a housing 12. The housing may include multiple components, such as an upper member 14 attached to a bottom member 16. The particular shape and construction of the housing 12 is not a limiting feature of the invention, and may be aesthetically pleasing configuration.

The device 10 may include a lancet 11 configured at one end thereof to provide the user with a means to draw a blood sample. The lancet 11 may include any manner of spring-loaded or stationary needle that is protected by a removable cover 19 prior to use. The needle is used to pierce the user's skin to provide the desired blood sample. It should be appreciated that the lancet 11 is an optional feature, and that the blood sample may be drawn by any conventional means or separate device. Additionally, a lancet would not be needed for applications that do not involve a blood sample.

The housing 12 may include a first window or viewing port 13 that indicates a "sample ready" condition of a sample meter 100 that is inserted into the device for analysis. This feature may be desired in that it informs the user when the test is ready to be conducted. Various means may be used to indicate the "ready" state. For example, dye chemistry may be used wherein a water soluble dye or coloring agent is applied to a section of the sample meter (i.e., at the end of the blood separation membrane, as discussed below). When the serum/plasma has migrated through the dye spot, the dye is "activated" and gives a visible indication to the user that the sample is ready for testing.

The housing may also include any manner of window or viewing port 15 to indicate the results of the test. For example, this window 15 may be disposed over a portion of a test strip 18 within the housing 12 that gives a visible "positive" or "negative" indication (e.g., by color change, line formation, graphics, and so forth) after reacting with the serum/plasma transferred from the sample meter 100. This test strip 18 is discussed in greater detail below, but includes a reactive membrane 20 having a detection region 31 and a collection region 30, as described in greater detail below. In a more sophisticated embodiment, the window 15 may display results of an electronic analysis of the sample. It should be appreciated that the device 10 is not limited by the manner in which the results are displayed to the user.

Figure 2A:
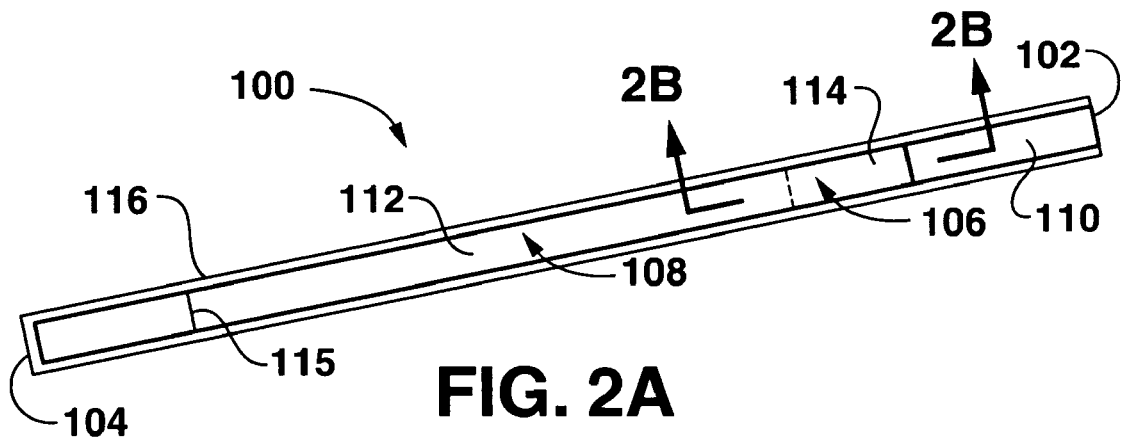
FIGS. 2A and 2B are a top perspective and cross-sectional view, respectively, of a sample meter.
Figure 2B:
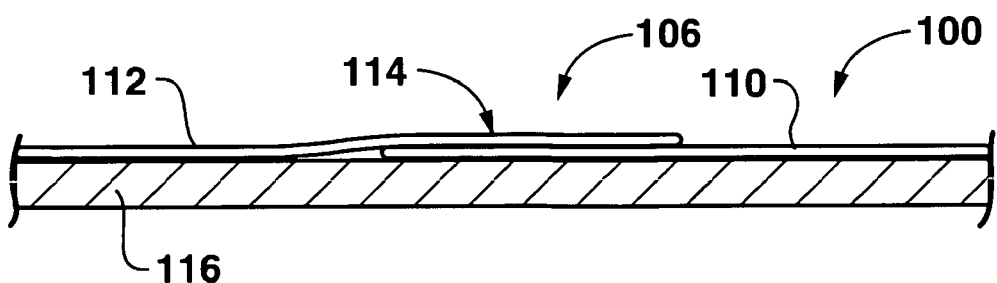

Referring to FIGS. 2A and 2B, an exemplary sample meter 100 is provided having a first end 102 for absorption of a test sample, such as blood, an opposite end 104, a filter section 106 adjacent the first end 102 that filters red blood cell components from the blood sample, and a storage section 108 adjacent the filtering section 106 that receives the plasma or serum from the filtering section 106. An opening 17 in the housing 12, for example in a side of the housing, is sized for insertion of the sample meter 100 into the housing 12 such that the storage section 108 of the sample meter 100 is disposed adjacent to the collection region 30 of membrane 20. The storage section 108 is brought into fluid communication with the collection region 30 of the membrane 20 (by direct contact or through an intermediary member) and the filtered plasma or serum is transferred from the storage section 108 to the collection region 30 of the membrane 20 for subsequent migration to the detection region 31. A diluent may be supplied to the collection region 30 to facilitate flow of the test sample from the collection region 30 to the detection region 31.

The combination of the sample meter 100 and test strip 18 (with membrane 20) is particularly effective for embodiments in which the blood test sample has a relatively low volume, such as less than about 10 microliters, in some embodiments less than about 5 microliters, and in some embodiments, between about 1 and about 3 microliters. For example, whole blood drops obtained from patients with a lancet from low-pain areas having reduced nerve endings as compared to a fingertip, such as the forearm, thigh, or other alternate sites, may have a volume of less than about 5 microliters. Despite such low volumes, the device and method of the present invention is effective in separating red blood cell components and providing a filtered test sample of plasma or serum that may be accurately analyzed for the presence of an analyte using lateral flow detection techniques.

In general, the membrane 20 may be made from any of a variety of materials through which the test sample is capable of passing. For example, the membrane 20 may be formed from natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. Particularly desired materials for forming the membrane 20 include polymeric materials, such as nitrocellulose, polyether sulfone, polyethylene, nylon, polyvinylidene fluoride, polyester, and polypropylene. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the test strip may generally vary as is readily recognized by those skilled in the art. For instance, the test strip 18 may have a length of from about 10 to about 100 millimeters, in some embodiments from about 20 to about 80 millimeters, and in some embodiments, from about 40 to about 60 millimeters. The width of the strip 18 may also range from about 0.5 to about 20 millimeters, in some embodiments from about 1 to about 15 millimeters, and in some embodiments, from about 2 to about 10 millimeters. Although not required, the thickness of the membrane 20 may be small enough to allow transmission-based detection. For example, the membrane may have a thickness less than about 500 micrometers, in some embodiments less than about 250 micrometers, and in some embodiments, less than about 150 micrometers.

As stated above, the test strip 18 includes a support 21 for the membrane 20. For example, the support 21 may be positioned directly adjacent to the membrane 20 as shown in the various figures, or one or more intervening layers may be positioned between the membrane 20 and the support 21. Regardless, the support 21 may generally be formed from any material able to carry the membrane 20. The support 21 may be formed from a material that is transmissive to light, such as transparent or optically diffuse (e.g., translucent) materials.

Also, it is generally desired that the support 21 is liquid-impermeable so that fluid flowing through the membrane 20 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth.

To provide a sufficient structural backing for the membrane 20, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane having a thickness of about 125 micrometers may be obtained from Millipore Corp. of Bedford, Mass. under the name "SHF180UB25."

The membrane 20 may be cast onto the support 21, wherein the resulting laminate may be die-cut to the desired size and shape. Alternatively, the membrane 20 may simply be laminated to the support 21 with, for example, an adhesive. In some embodiments, a membrane (e.g., nitrocellulose or nylon) is adhered to a Mylar® film. An adhesive is used to bind the membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, III, et al., which is incorporated herein in its entirety by reference thereto for all purposes.

The device 10 may also contain an absorbent pad (not shown) within the housing 12 positioned adjacent to or near an end of the membrane 20. The absorbent pad generally receives fluid that has migrated through the entire membrane 20, and may assist in promoting capillary action and fluid flow through the membrane 20.

As mentioned, the membrane 20 includes the collection region 30, which is the portion of the membrane disposed to receive the metered portion of the test sample from the sample meter 100. The collection region 30 collects and temporarily stores the test sample before the sample is conducted to a detection region 31, as described in greater detail below.

In the particular embodiments illustrated in the figures, the sample meter 100 includes a separation membrane 110 at the filter section 106. This separation membrane 110 is selected from a known class of materials capable of filtering red blood cell components from fluids, examples of which are provided below. The sample meter 100 includes a storage membrane 112 disposed to receive filtered plasma or serum from the separation membrane 110. For example, in a particular arrangement of the materials, the separation membrane 110 and storage membrane 112 overlap along at least a portion of their length in an overlap region 114 depicted for example in FIG. 2B. In this overlap region 114, filtered plasma or serum is transferred from the separation membrane 110 to the storage membrane 112.

It should be appreciated that the sample meter 100, or its constituent membrane components 110, 112, are not limited by dimensions or shape. For example, the separation membrane 110 may have a length of between about 3 to about 12 mm. The overlap region 114 between the separation and storage membranes may be between about 1 mm to about 3 mm. The storage membrane 112 may have a length of between about 10 mm to about 40 mm. In a particular embodiment, the sample meter 100 has the elongated strip shape illustrated in the figures with a width of between about 1 mm to about 5 mm, and a total length of between about 25 mm to about 40 mm. The separation membrane 110 may extend to the first end 102 of the meter 100, and the storage membrane 112 may extend to the opposite second end 104 of the meter 100.

The storage membrane 112 may comprise any material through which test samples are capable of passing. For example, the storage membrane 112 may be formed from any of the natural, synthetic, or naturally occurring materials identified above as suitable for use as membrane 20. A particularly useful material is a nitrocellulose membrane (e.g., Millipore Inc. HF 120 or 75).

The separation membrane 110 may be any suitable material, for example, a hydrophobic material capable of filtering cells (e.g., blood cells) from fluids. Various packings or sieving depth filters may be employed, such as glass fibers, cellulose or glass filters treated with red blood cell capture reagents, glass fiber filters, synthetic fiber filters or a composite material including any combination of the above materials. Glass fiber filters, for instance, are commercially available from Whatman plc of Kent, United Kingdom; Millipore Corp. of Billerica, Mass.; and Pall Corp. of Ann Arbor, Mich. Such glass fiber filters may have a fiber diameter in the range of about 0.05 to about 9 micrometers and a density of about 50 to about 150 g/m$^2$. Other examples of suitable blood separation filters are described in U.S. Pat. No. 5,416,000 to Allen, et al., as well as U.S. Patent Application Publication Nos. 2004/0126833 to Shull, et al. and 2003/0032196 to Zhou, all of which are incorporated herein in their entirety by reference thereto for all purposes. If desired, the blood separation filter may be treated with one or more reagents (e.g., agglutinin), such as described above. In a particular embodiment, a useful separation membrane is vertical blood separation membrane from PALL Inc. identified as "BTS SP 300."

To add structural rigidity and additional functionality to the sample meter 100, it may be desired to attach the separation and storage membranes 110, 112 to a backing strip 116, as particularly illustrated in FIGS. 2A and 2B. Preferably, this backing strip 116 is a generally transparent material so that migration of the blood plasma or serum to the storage section 108 of the meter 100 may be observed through the backing strip material 116.

The sample meters 100 may be made with various processing steps. In a particular embodiment, material such as Millipore nitrocellulose HF 75 or HF 120 may be laminated onto a transparent card material that serves as the backing strip 116. A separate piece of blood separation material serving as the separation membrane 110 may then be laminated onto the transparent card material with the desired overlap between it and the storage membrane material. The card with laminated materials may then be processed through a Kinematic slitter from Kinematic Automation, Inc., or other suitable cutting device, to cut the assembled card into strips having a desired width dimension (e.g. 1 mm, 2 mm, or so forth). It should be readily appreciated that economical mass production of the sample meters 100 is possible, and is contemplated within the scope and spirit of the invention.

As mentioned, after the sample meter 100 has been used to collect a suitable sample and separate plasma or serum from the blood sample, the meter 100 may be inserted into a lateral flow assay device such that the storage section 108 lies adjacent to the membrane 20. This configuration is depicted generally in FIG. 1. Referring to FIGS. 4A and 4B, the sample meter 100 is inserted so as to lie above the membrane 20 from where it is subsequently pushed into contact with the membrane 20. In alternate embodiments, the sample meter 100 may lie below the membrane 20.

Figure 6:
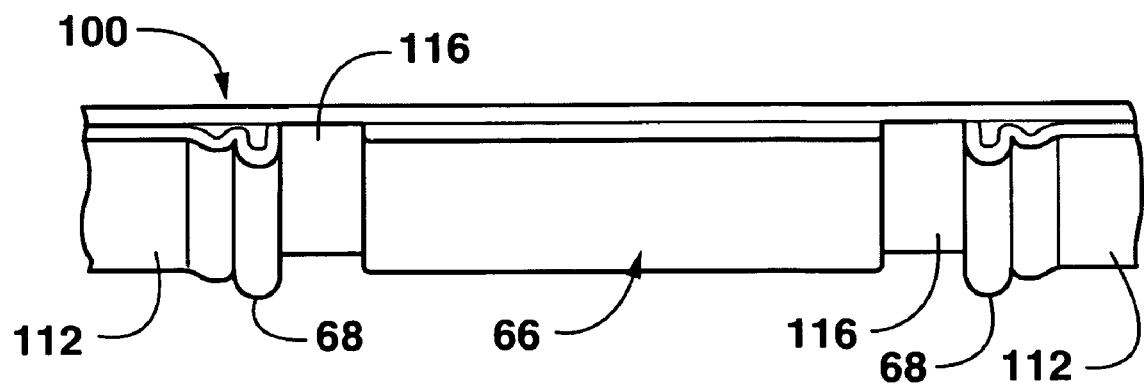
FIG. 6 is a perspective view of a sample meter that has been scored and scraped with a device according to aspects of the invention.

In order to provide a precisely determined volume of the test sample to the test strip 18, the device 10 includes an internal scraping mechanism 40. The scraping mechanism 40 is configured to score and scrape the sample meter 100 so that a well defined length 66 (FIG. 6) of the sample meter is formed and presented to the collection region 30 of the test strip 18. Referring to the various figures, the mechanism 40 scores the storage membrane 112 at locations that determine the length of the defined length section 66. The mechanism 40 scores the membrane 112 to the backing strip 116 and then "pushes" the margin portions 68 of the membrane 112 away from the defined length portion 66 so that the defined length portion 66 is no longer in fluid communication with the margin portions 68. The length of the defined length section 66 may be, for example, 5 mm, or any other desired length. The section 66 is saturated with the test sample fluid and, thus, based on the known saturation volume of the defined length section 66, a precisely determined amount of the test sample fluid is known and presented to the collection region 30 of the test strip 18.

An embodiment of the scraping mechanism 40 is illustrated in FIGS. 3A through 5. In this particular embodiment, the mechanism 40 includes a pair of spaced apart and movably mounted blades 42. The blades 42 may be pivotally mounted relative to a common axis 44, as particularly illustrated in FIGS. 4A and 4B. In a first static position illustrated in FIG. 4A, the blades 42 are disposed below the membrane surface side of the sample meter 100 and are spaced apart a distance that defines the length of the defined length section 66. In a second actuated position illustrated for example in FIG. 4B, the blades contact and score the membrane side of the sample member 100 as they pivot in opposite directions to scrape the side margins 68 away from the defined length section 66.

The blades 42 may be mounted relative to the common longitudinal axis 44 on opposite longitudinal sides of the test strip 18, as particularly illustrated in FIGS. 4A and 4B, and configured to rotate away from the test strip 18 in the second actuated position of the blades 42, as illustrated in FIG. 4B. In this particular embodiment, the sample meter 100 may be disposed generally perpendicular to the test strip 18 so as to be disposed across the blades 42.

Figure 5:
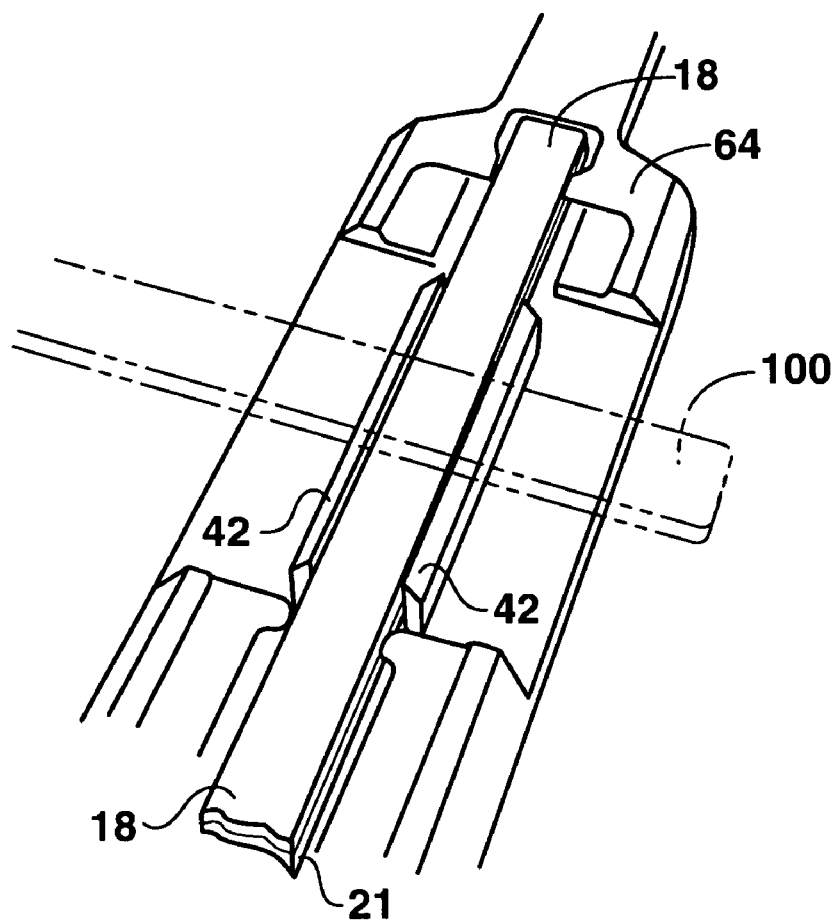
FIG. 5 is a perspective view of a tray component used to retain the test strip in particular embodiment of the invention.

FIG. 5 illustrates an internal tray 64 that may be configured to house the test strip 18 and blades 42. As can be seen in this figure, the test strip 18 is disposed longitudinally along the tray 64 between the blades 42. The sample meter 100 is depicted in phantom lines disposed above the blades 42 perpendicular to the test strip 18.

In the illustrated embodiment, the test strip 18 is disposed below the sample meter 100 and a manually actuated device 46 is configured on the housing to move the blades 42 from their static position to the actuated position discussed above. This manually actuated device 46 may take on any suitable form, and may be, for example, a manual push or slide button 48 as illustrated in the figures. Motion of this button 48 may be transmitted to an internal plunger mechanism that pushes the sample meter 100 into contact with the blades 42, as illustrated in FIGS. 4A and 4B. Transfer of motion from the button 48 to the plunger 50 may be achieved by any suitable means. For example, in the illustrated embodiment, the button 48 is a slide button that is moved along the surface of the housing 12. A cam track 54 is disposed on an underside of the button structure. A protrusion (not illustrated) of a component of the plunger 50 rides in the cam track 54, which causes the plunger 50 to move downward against the force of a biasing spring 52 as the plunger engages in the inclined cam slot 54. The plunger mechanism may include any manner of structure 56 that presses down on the sample meter 100, which causes the sample meter 100 to engage the blades 42 and to push the blades to their actuated position illustrated in FIG. 4B.

In an alternative embodiment, the manual button 48 may be a type of button that is simply depressed in a vertical direction, resulting in structure 56 beneath the button engaging against the sample meter 100. It should be appreciated that any manner of manually actuated devices may be configured for the purpose of moving the sample meter 100 against the blades 42.

Figure 3A:
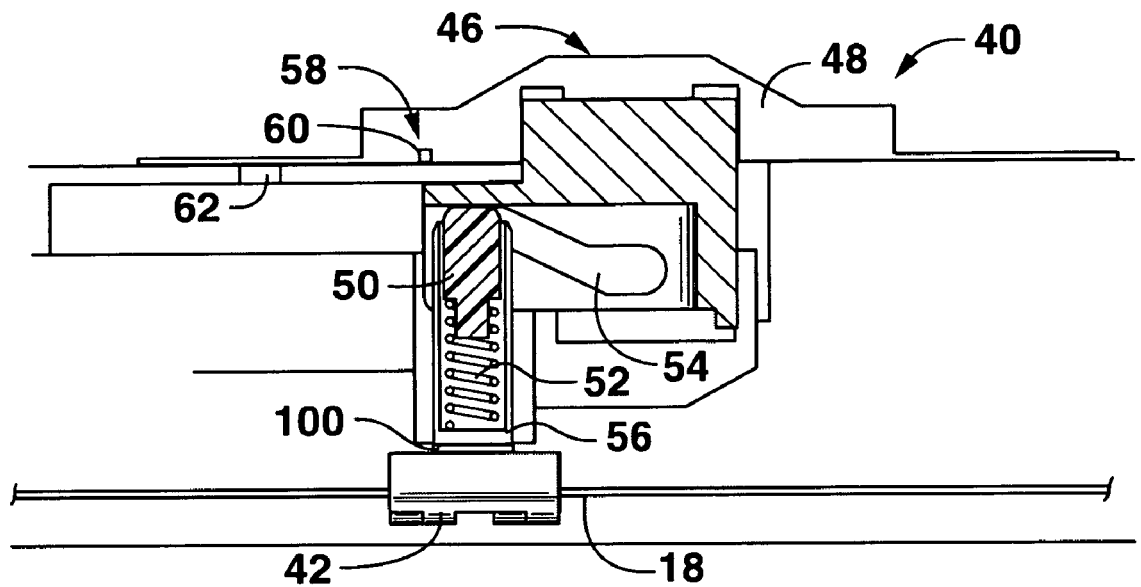
FIGS. 3A and 3B are cross-sectional operational views of an embodiment of a scraping mechanism that may be used in an assay device according to the invention.
Figure 3B:
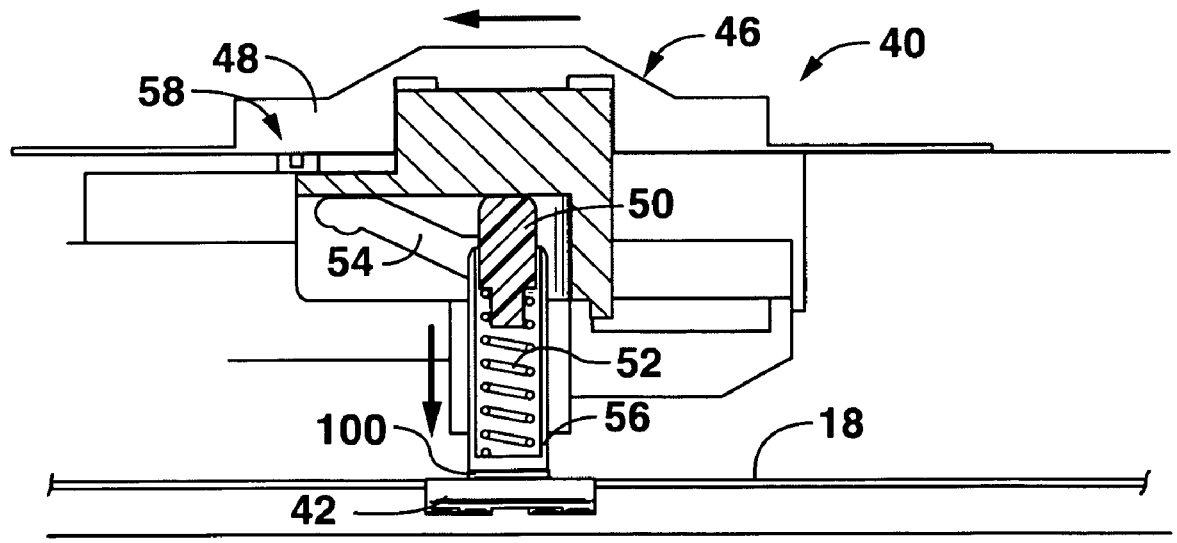

Motion of the button 48 and associated plunger mechanism 50 also serves to press the defined length section 66 of the sample meter 100 against the collection region 30 of the underlying test strip 18. To facilitate transfer of the test sample from the defined length section 66 to the test strip 18, a diluent may be introduced, as described in greater detail below. During this transfer, however, it is generally desired to maintain the defined length section 66 in contact against the collection region of the test strip 18. For this purpose, any suitable latch mechanism 58 may be used to maintain the manually actuated device 46 (e.g., button 48) in a position that maintains the sample meter 100 against the test strip 18. In one embodiment, a suitable latch mechanism 58 may include, for example, a spring loaded protrusion 60 provided on an underside of the slide button 48 that engages into a recess 62 defined in the upper surface of the housing 12, as schematically depicted in FIGS. 3A and 3B. It should be appreciated that any manner of suitable latching or stop mechanism may be used in this regard.

Regardless of the particular mechanism or method used to position and isolate a portion of the sample meter 100 relative to the membrane 20, a diluent (or washing agent) is generally employed upstream to facilitate delivery of the test sample from the storage section 108 of the meter 100 to the collection region 30 of the membrane 20.

The diluent may be any material having a viscosity that is sufficiently low to allow movement of the fluid by capillary action and that supports a reaction between the analyte and any binding agents (e.g., does not interfere with antibody/antigen interaction). In one embodiment, the diluent contains water, a buffering agent; a salt (e.g., NaCl); a protein stabilizer (e.g., BSA, casein, trehalose, or serum); and/or a detergent (e.g., nonionic surfactant). Representative buffering agents include, for example, phosphate-buffered saline (PBS) (e.g., pH of 7.2), 2-(N-morpholino) ethane sulfonic acid (MES) (e.g., pH of 5.3), HEPES buffer, TBS buffer, etc., and so forth.

Figure 7:
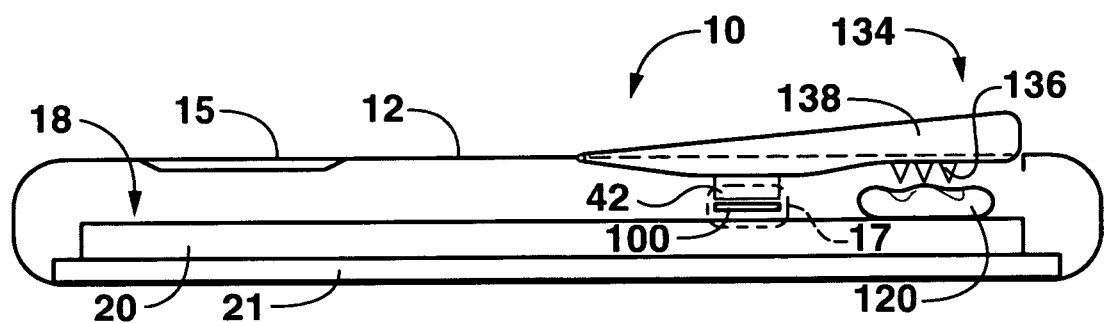
FIG. 7 is a cross-sectional view of an alternative embodiment of an assay device according to the invention.

The assay device 10 may incorporate an internal source of diluent that is applied so as to flow to the collection region subsequent to insertion of the sample meter 100 into the assay housing 12 and scraping of the meter 100 to provide the defined length of meter. For example, referring to FIG. 7, an internal diluent source is illustrated as a pouch or container 120 having the diluent contained therein. Means 134 are provided for rupturing or otherwise breaching the pouch 120 subsequent to or coincident with scraping of the sample meter 100. This means may be configured to operate simultaneously with the scraping mechanism 40, and may be actuated by the same manual button or slide 48. For example, in the embodiment illustrated in FIG. 7, the means 134 includes a push button mechanism 138 or other manually actuated device that is readily configured with the assay housing 12. In this embodiment, the pivotal blades 42 are configured so as to be pressed down onto the sample meter 100 upon the clinician activating the device 10 by pushing in the button 138. The pivotal blades 42 are brought into contact with the sample meter 100 and scrape the sample so as to define the metered length 66 of the sample meter 100, as well as pressing the sample meter into fluid contact with the underlying membrane 20. Points or a blade 136 may be provided on the push button mechanism 138 and disposed so as to pierce the internal pouch 120 causing the diluent to flow towards the collection region of the membrane 20. Sustained depression of the mechanism 138 may also serve to compress the pouch 120 and force the diluent therefrom in the direction of the collection region 30 of the membrane 20, as well as ensure that the sample meter 100 remains in contact with the membrane.

In an alternative embodiment, a separate actuating device may be provided for rupturing the internal diluent source 120, such as a separate push button that is actuated after the scraping mechanism 40. It should be appreciated that any number of manually actuated devices may be readily configured by those skilled in the art for the purpose of rupturing an internal source of diluent within the assay housing 12, and all such devices are within the scope and spirit of the invention.

Figure 8:
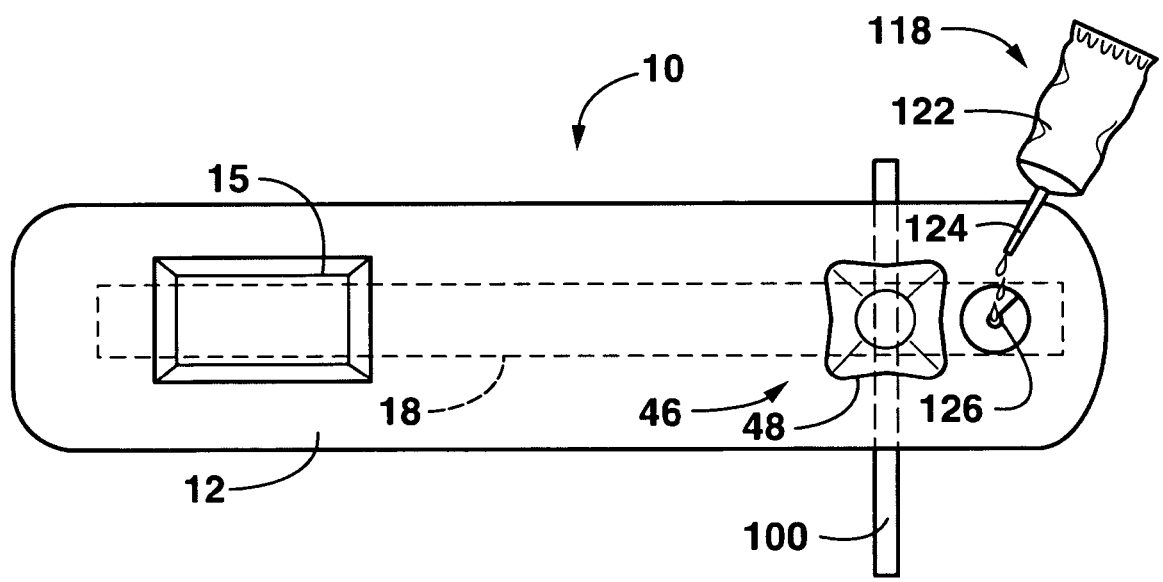
FIG. 8 is a top view of still another embodiment of an assay device according to the invention.

In an alternate embodiment illustrated, for example in FIG. 8, an external diluent source 118 may be provided. In the illustrated embodiment, this external source is illustrated as a capsule 122 or other disposable container, preferably a squeezable container having a nozzle 124 configured for insertion into a port 126 defined in the assay housing 12. The port 126 is disposed so that the diluent is supplied upstream of the sample meter 100 and caused to flow towards the collection region of the membrane 20. Internal diluent directing structure, such as channels or the like, may be defined within the housing 12 to more precisely direct the diluent to the desired location.

In addition to the components set forth above, the diagnostic test kit of the present invention may also contain various other components to enhance detection accuracy. For exemplary purposes only, one embodiment of an immunoassay that may be performed in accordance with the present invention to detect the presence of an analyte will now be described in more detail. Immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

To facilitate the detection of the analyte within the test sample, a substance may be pre-applied to the sample meter 100, or previously mixed with the diluent or test sample, which is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. Nos. 5,670,381 to Jou, et al. and 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. Nos. 6,261,779 to Barbera-Guillem, et al. and 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and II, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. Nos. 4,614,723 to Schmidt, et al.; 5,464,741 to Hendrix; 5,518,883 to Soini; 5,922,537 to Ewart, et al.; 6,004,530 to Sagner, et al.; and 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2,2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2,2'bipyridine)ruthenium (II); (2,2'-bipyridine)[bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'- bipyridine-4'-butylamide ruthenium (II), and so forth. Still other suitable metal complexes that may exhibit phosphorescent properties may be described in U.S. Pat. Nos. 6,613,583 to Richter, et al.; 6,468,741 to Massey, et al.; 6,444,423 to Meade, et al.; 6,362,011 to Massey, et al.; 5,731,147 to Bard, et al.; and 5,591,581 to Massey, et al., which are incorporated herein in their entirety by reference thereto for all purposes.

In some cases, luminescent compounds may have a relatively long emission lifetime may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (III)). Such chelates may exhibit strongly redshifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is longlived, with lifetimes of about 100 to about 1000 microseconds, as compared to about 1 to about 100 nanoseconds for other fluorescent labels. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. Nos. 6,030,840 to Mullinax, et al.; 5,585,279 to Davidson; 5,573,909 to Singer, et al.; 6,242,268 to Wieder, et al.; and 5,637,509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. Nos. 5,670,381 to Jou, et al.; 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In some instances, it may be desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte (i.e., "analog") may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, such as with poly(thiophenol), the detection probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino)ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption or chemisorption, may also be utilized in the present invention.

Referring again to the figures in general, after passing through the collection region 30 of the test strip 18, the diluent and test sample travel through the membrane 20 until reaching the detection zone 31. Upon reaching the detection zone 31, the volume of the test sample is relatively uniform across the entire width of the detection zone 31. In addition, as a result of the known saturation volume of the defined length 66 of the sample meter 100 defined by the scraping mechanism 40, the volume of the test sample is also predetermined within a narrow range.

Within the detection zone 31, a receptive material is immobilized that is capable of binding to the conjugated detection probes. The receptive material may be selected from the same materials as the specific binding members described above, including, for instance, antigens; haptens; antibody-binding proteins, such as protein A, protein G, or protein A/G; neutravidin (a deglycosylated avidin derivative), avidin (a highly cationic 66,000-dalton glycoprotein), streptavidin (a nonglycosylated 52,800-dalton protein), or captavidin (a nitrated avidin derivative); primary or secondary antibodies, and derivatives or fragments thereof. In one embodiment, for example, the receptive material is an antibody specific to an antigen within the test sample. The receptive material serves as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized first receptive material. Upon being bound to the immobilized receptive material, the complexed probes form a new ternary sandwich complex.

Other than the detection zone 31, the membrane 20 may also define various other zones for enhancing detection accuracy. For example, in embodiments in which high analyte concentrations are a concern, the assay device 20 may contain an indicator zone 33 that is positioned downstream from the detection zone 31 and is configured to provide information as to whether the analyte concentration has reached the saturation concentration ("hook effect" region) for the assay. The indicator zone 33 contains a second receptive material that is immobilized on the membrane 23 and serves as a stationary binding site for the conjugated detection probes. To accomplish the desired binding within the indicator zone 33, it is generally desired that the second receptive material is capable of differentiating between those detection probes that are complexed with the analyte and those that remain uncomplexed. For example, in one embodiment, the second receptive material includes a molecule that has at least one epitope in common with the analyte, such as analyte molecules, or derivatives or fragments (i.e., analog) thereof, so that it is capable of specifically binding to an antibody conjugate when it is uncomplexed with the analyte.

Alternatively, the second receptive material may include a biological material that is not an analyte molecule or analog thereof, but nevertheless is capable of preferentially binding to uncomplexed conjugated detection probes. In one embodiment, for example, the first receptive material may be a monoclonal antibody, such as anti-CRP $IgG_1$. The detection probes are conjugated with a monoclonal antibody different than the monoclonal antibody of the first receptive material, such as anti-CRP $IgG_2$. In this particular embodiment, the second receptive material may be a secondary antibody, such as Goat anti-human, IgG $F(ab')_2$, which has been adsorbed against $F_c$ fragments and therefore reacts only with the $F_{ab}$ portion of IgG. Thus, when no analyte is present, the secondary antibody is able to bind to the free "$F_{ab}$" binding domain of the anti-CRP $IgG_2$ monoclonal antibody. However, when an antigen is present in the test sample, it first complexes with the "$F_{ab}$" binding domain of the anti-CRP $IgG_2$ monoclonal antibody. The presence of the antigen renders the "$F_{ab}$" binding domain unavailable for subsequent binding with the secondary antibody. In this manner, the secondary antibody within the indicator zone 33 is capable of preferentially binding to uncomplexed detection probes.

Although the detection zone 31 and optional indicator zone 33 may provide accurate results, it is sometimes difficult to determine the relative concentration of the analyte within the test sample under actual test conditions. Thus, the test strip 18 may include a calibration zone 32 that is positioned downstream from the detection zone 31 and optional indicator zone 33. Alternatively, however, the calibration zone 32 may also be positioned upstream from the detection zone 31 and/or optional indicator zone 33. The calibration zone 32 is provided with a third receptive material that is capable of binding to any calibration probes that pass through the length of the membrane 20. When utilized, the calibration probes may contain a detectable substance that is the same or different than the detectable substance used for the detection probes. Moreover, the calibration probes may also be conjugated with a specific binding member, such as described above. For example, in one embodiment, biotinylated calibration probes may be used. Generally speaking, the calibration probes are selected in such a manner that they do not bind to the first or second receptive material at the detection zone 31 and indicator zone 33. The third receptive material of the calibration zone 32 may be the same or different than the receptive materials used in the detection zone 31 or indicator zone 33. For example, in one embodiment, the third receptive material is a biological receptive material, such as antigens, haptens, antibody-binding proteins (e.g., protein A, protein G, or protein A/G), neutravidin, avidin, streptavidin, captavidin, primary or secondary antibodies, or complexes thereof. It may also be desired to utilize various non-biological materials for the third receptive material (e.g., polyelectrolytes) of the calibration zone 32, such as described in U.S. Patent Application Publication No. 2003/0124739 to Song, et al., which is incorporated herein in its entirety by reference thereto for all purposes.

When utilized, the polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly(dimethylamine-co-epichlorohydrin); polydiallyidimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridnium iodide) and poly(styryl-b-acrylic acid), both of which are available from Polymer Source, Inc. of Dorval, Canada.

Although any polyelectrolyte may generally be used, the polyelectrolyte selected for a particular application may vary depending on the nature of the detection probes, the calibration probes, the membrane, and so forth. In particular, the distributed charge of a polyelectrolyte allows it to bind to substances having an opposite charge. Thus, for example, polyelectrolytes having a net positive charge are often better equipped to bind with probes that are negatively charged, while polyelectrolytes that have a net negative charge are often better equipped to bind to probes that are positively charged. Thus, in such instances, the ionic interaction between these molecules allows the required binding to occur within the calibration zone 32. Nevertheless, although ionic interaction is primarily utilized to achieve the desired binding in the calibration zone 32, polyelectrolytes may also bind with probes having a similar charge.

Because the polyelectrolyte is designed to bind to probes, it is typically desired that the polyelectrolyte be substantially non-diffusively immobilized on the surface of the membrane 20. Otherwise, the probes would not be readily detectable by a user. Thus, the polyelectrolytes may be applied to the membrane 20 in such a manner that they do not substantially diffuse into the matrix of the membrane 20. In particular, the polyelectrolytes typically form an ionic and/or covalent bond with functional groups present on the surface of the membrane 20 so that they remain immobilized thereon. Although not required, the formation of covalent bonds between the polyelectrolyte and the membrane 20 may be desired to more permanently immobilize the polyelectrolyte thereon. For example, in one embodiment, the monomers used to form the polyelectrolyte are first formed into a solution and then applied directly to the membrane 23. Various solvents (e.g., organic solvents, water, etc.) may be utilized to form the solution. Once applied, the polymerization of the monomers is initiated using heat, electron beam radiation, free radical polymerization, and so forth. In some instances, as the monomers polymerize, they form covalent bonds with certain functional groups of the membrane 20, thereby immobilizing the resulting polyelectrolyte thereon. For example, in one embodiment, an ethyleneimine monomer may form a covalent bond with a carboxyl group present on the surface of some membranes (e.g., nitrocellulose).

In another embodiment, the polyelectrolyte may be formed prior to application to the membrane 20. If desired, the polyelectrolyte may first be formed into a solution using organic solvents, water, and so forth. Thereafter, the polyelectrolytic solution is applied directly to the membrane 20 and then dried. Upon drying, the polyelectrolyte may form an ionic bond with certain functional groups present on the surface of the membrane 20 that have a charge opposite to the polyelectrolyte. For example, in one embodiment, positively-charged polyethyleneimine may form an ionic bond with negatively-charged carboxyl groups present on the surface of some membranes (e.g., nitrocellulose).

In addition, the polyelectrolyte may also be crosslinked to the membrane 23 using various well-known techniques. For example, in some embodiments, epichlorohydrin-functionalized polyamines and/or polyamidoamines may be used as a crosslinkable, positively-charged polyelectrolyte. Examples of these materials are described in U.S. Pat. Nos. 3,700,623 to Keim and 3,772,076 to Keim, 4,537,657 to Keim, which are incorporated herein in their entirety by reference thereto for all purposes and are believed to be sold by Hercules, Inc., Wilmington, Del, under the Kymene™ trade designation. For instance, Kymene™ 450 and 2064 are epichlorohydrin-functionalized polyamine and/or polyamidoamine compounds that contain epoxide rings and quaternary ammonium groups that may form covalent bonds with carboxyl groups present on certain types of membranes (e.g., nitrocellulose) and crosslink with the polymer backbone of the membrane when cured. In some embodiments, the crosslinking temperature may range from about 50° C. to about 120° C. and the crosslinking time may range from about 10 to about 600 seconds.

Although various techniques for non-diffusively immobilizing polyelectrolytes on the membrane 20 have been described above, it should be understood that any other technique for non-diffusively immobilizing polyelectrolytic compounds may be used in the present invention. In fact, the aforementioned methods are only intended to be exemplary of the techniques that may be used in the present invention. For example, in some embodiments, certain components may be added to the polyelectrolyte solution that may substantially inhibit the diffusion of such polyelectrolytes into the matrix of the membrane 20.

The detection zone 31, indicator zone 33, and calibration zone 32 may each provide any number of distinct detection regions so that a user may better determine the concentration of one or more analytes within a test sample. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the test strip 18. Likewise, in some embodiments, the regions may be disposed in the form of lines in a direction that is substantially parallel to the flow of the test sample.

In some cases, the membrane 20 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 20, but is preferably positioned downstream from the detection zone 31 and the indicator zone 33.

Qualitative, semi-quantitative, and quantitative results may be obtained in accordance with the present invention. For example, when it is desired to semi-quantitatively or quantitatively detect an analyte, the intensity of any signals produced at the detection zone 31, indicator zone 33, and/or calibration zone 32 may be measured with an optical reader. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the intensity of a fluorescence signal. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to signal intensity.

Although various embodiments of device configurations have been described above, it should be understood, that a device of the present invention may generally have any configuration desired, and need not contain all of the components described above. Various other device configurations, for instance, are described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

Various assay formats may also be used to test for the presence or absence of an analyte using the assay device of the present invention. For instance, a "sandwich" format typically involves mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described by U.S. Pat. Nos. 4,168,146 to Grubb, et al. and 4,366,241 to Tom, et al., which are incorporated herein in their entirety by reference thereto for all purposes. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., 4,442,204 to Liotta, and 5,208,535 to Buechler, et al., which are incorporated herein in their entirety by reference thereto for all purposes. Various other device configurations and/or assay formats are also described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

As a result of the present invention, a controlled volume of a test sample may be uniformly delivered to a detection zone of a lateral flow assay device. Such control over sample flow provides a significant improvement in detection accuracy and sensitivity for lateral flow systems. One particular benefit is that sample application and testing may be done in a relatively quick, easy, and simple manner. Further, as a result of the controlled flow provided by the present invention, low volume test samples may be accurately tested without the requirement of complex and expensive equipment to obtain a useable sample. For example, whole blood drops having a volume of about 5 microliters or less may be readily analyzed for the presence of an analyte in accordance with the present invention.

What is claimed is:

1. A lateral flow assay device that further includes:
    a housing, and a test strip disposed within said housing comprising a membrane with a detection region and a collection region;
    a sample meter comprising a first end for absorption of a test sample, and a storage section that receives and stores at least a component of the test sample;
    an opening in said housing sized for insertion of said sample meter into said housing such that said storage section of said sample meter is disposed adjacent said collection region of said membrane, the test sample component transferable from said storage section to said collection region for subsequent migration to said detection region; and
    an activatable isolation mechanism within said housing and disposed so as to physically detach from said sample meter a defined length of said sample meter storage section upon activation thereof such that said detached defined length of said storage section is presented to said collection region of said membrane.

2. The assay device as in claim 1, wherein said sample meter is a blood sample meter and includes a filtering section adjacent said first end that filters red blood cell components from a blood sample such that said storage section receives plasma or serum components of the blood sample.

3. The assay device as in claim 2, wherein said blood sample meter comprises a separation membrane attached to a storage membrane with an overlap between said separation and storage membranes in said filtering section.

4. The assay device of claim 1, further comprising a source of diluent stored in a rupturable container within said housing, and further comprising a manually activated rupturing mechanism that ruptures said container subsequent to insertion of said sample meter into said housing.

5. The assay device of claim 4, wherein said rupturing mechanism is configured with said scraping mechanism so as to be activated generally simultaneously therewith.

6. The assay device of claim 4, wherein said rupturing mechanism is configured separate from said scraping mechanism so as to be activated separately therefrom.

7. The assay device of claim 1, further comprising a source of diluent external to said housing, said housing further comprising a port for communication with said external diluent source.

8. A lateral flow assay device that further includes:
a housing, and a test strip disposed within said housing comprising a membrane with a detection region and a collection region;
a sample meter comprising a first end for absorption of a test sample, and a storage section that receives and stores at least a component of the test sample;
an opening in said housing sized for insertion of said sample meter into said housing such that said storage section of said sample meter is disposed adjacent said collection region of said membrane, the test sample component transferable from said storage section to said collection region for subsequent migration to said detection region; and
an activatable isolation mechanism within said housing and disposed so as to isolate portions of said sample meter storage section upon activation thereof such that a defined length of said storage section is presented to said collection region of said membrane,
wherein said isolation mechanism comprises a scraping mechanism having a pair of spaced apart and movably mounted blades, said blades contacting said sample meter at a first static position that defines said defined length of said storage section between said blades, said blades scraping said storage section on opposite sides of said defined section as said blades move to a second actuated position.

9. The assay device as in claim 8, wherein said blades are pivotally mounted along a respective longitudinal axis on opposite longitudinal sides of said test strip and rotate away from said test strip in said second actuated position, said sample meter disposed generally across said blades perpendicular to said test strip.

10. The assay device as in claim 9, further comprising a manually actuated device configured on said housing that causes said blades to move from said static position to said actuated position.

11. The assay device as in claim 10, wherein said manually actuated device comprises a spring biased plunger that contacts and pushes said sample meter against said blades.

12. The assay device as in claim 11, wherein said test strip is disposed below said sample meter, said plunger pushing said sample meter into contact with said test strip subsequent to scraping of said sample meter.

13. The assay device as in claim 12, further comprising a latch that maintains said plunger in said second actuated position so that said sample meter is maintained in contact with test strip.

14. A method for performing a lateral flow assay on a test sample of less than about 10 microliters to detect the presence of an analyte in the test sample, the method comprising:
exposing an end of a sample meter to the test sample, the sample meter absorbing the sample, separating certain components from the sample, and saving the remaining portion of the sample in a storage section of the sample meter;
inserting the sample meter into a lateral flow assay device having a test strip with a collection region and a detection region;
physically detaching a part of the storage section of the sample meter so as to define a metered length of the storage section;
presenting the metered length of the storage section in fluid communication with the collection region of the test strip while supplying a diluent to the collection region; and
whereby the sample is transferred from the metered length of the storage section of the sample meter to the collection region of the membrane and migrates to the detection region of the membrane.

15. The method as in claim 14, further comprising supplying the diluent generally simultaneously with said isolating of the storage section of the sample meter.

16. The method as in claim 14, wherein the test sample is blood and the volume of the blood test sample is less than 5 microliters.

17. The method as in claim 16, wherein the volume of the blood test sample is between about 1 to about 3 microliters.

18. The method as in claim 14, comprising supplying the diluent from a source within the lateral flow assay device.

19. The method as in claim 14, comprising supplying the diluent from a source external to the lateral flow assay device.

20. The method as in claim 14, comprising pushing the metered length of the storage section into fluid communication with the collection region of the membrane immediately subsequent to said isolating of the storage section of the sample meter.

21. The method as in claim 14, wherein said isolating of the storage section comprises scoring and scraping away portions of the storage section to define the metered length of storage section.

* * * * *